United States Patent
Schweikert

(10) Patent No.: US 8,425,401 B2
(45) Date of Patent: Apr. 23, 2013

(54) GASTRIC INFLATION BAND WITH INTEGRATED INFUSION CATHETER

(75) Inventor: Timothy M. Schweikert, Levittown, PA (US)

(73) Assignee: Medical Components, Inc., Harleysville, PA (US)

(*) Notice: Subject to any disclaimer, the term of this patent is extended or adjusted under 35 U.S.C. 154(b) by 681 days.

(21) Appl. No.: 12/362,680

(22) Filed: Jan. 30, 2009

(65) Prior Publication Data

US 2009/0198261 A1     Aug. 6, 2009

Related U.S. Application Data

(60) Provisional application No. 61/024,603, filed on Jan. 30, 2008.

(51) Int. Cl.
*A61B 17/00* (2006.01)
(52) U.S. Cl.
USPC ............. 600/37; 606/151; 606/157; 604/909
(58) Field of Classification Search ............. 600/29–32, 600/37; 606/153, 155–157, 191, 201–203, 606/151; 128/897, 898; 604/892.1, 103.01, 604/103.02, 500–513, 9, 909
See application file for complete search history.

(56) References Cited

U.S. PATENT DOCUMENTS

| | | | |
|---|---|---|---|
| 4,549,879 A | 10/1985 | Groshong et al. | |
| 4,592,339 A | 6/1986 | Kuzmak et al. | |
| 4,634,443 A * | 1/1987 | Haber | 600/31 |
| 4,671,796 A | 6/1987 | Groshong et al. | |
| 4,701,166 A | 10/1987 | Groshong et al. | |
| 5,074,868 A | 12/1991 | Kuzmak | |
| 5,226,429 A | 7/1993 | Kuzmak | |
| 5,336,178 A * | 8/1994 | Kaplan et al. | 604/509 |
| 5,601,604 A | 2/1997 | Vincent | |
| 5,658,298 A | 8/1997 | Vincent et al. | |

(Continued)

FOREIGN PATENT DOCUMENTS

WO   WO2007048822   5/2007
WO   WO2006063593   6/2008

OTHER PUBLICATIONS

INAMED Health, BioEnterics® LAP-BAND® Adjustable Gastric Banding System, Jul. 2003, pp. 1 through 20.

(Continued)

*Primary Examiner* — Patricia Bianco
*Assistant Examiner* — Kari Petrik
(74) *Attorney, Agent, or Firm* — Blank Rome LLP

(57) ABSTRACT

An inflatable gastric band incorporates a fluid channel within an outer surface of the band and an inflatable bladder on a stomach-facing side of the band. The gastric band attaches to a double lumen catheter, which communicates with a dual infusion port. One lumen communicates with the fluid channel and one port, while the other lumen communicates with the inflatable bladder and a second port. Injection of fluid into one chamber of the infusion port expands inflatable bladder, allowing adjustment to the diameter of the stoma. Injection of drugs or therapeutic agents into the second chamber allows the infusion of drugs or agents directly into the abdominal cavity of a gastric band recipient. The inflatable bladder can be continuous or segmented. A segmented bladder reduces pinching and/or folding of the inner surface of the gastric band during expansion/contraction, thereby lessening stomach pinching and/or irritation.

12 Claims, 3 Drawing Sheets

U.S. PATENT DOCUMENTS

| | | | |
|---|---|---|---|
| RE36,176 E | 3/1999 | Kuzmak | |
| 5,910,149 A | 6/1999 | Kuzmak | |
| 5,938,669 A | 8/1999 | Klaiber et al. | |
| 6,491,623 B2* | 12/2002 | Snyder et al. | 600/31 |
| 7,037,344 B2 | 5/2006 | Kagan et al. | |
| 7,798,954 B2* | 9/2010 | Birk et al. | 600/37 |
| 7,811,298 B2* | 10/2010 | Birk | 606/157 |
| 7,899,540 B2* | 3/2011 | Maschino et al. | 607/40 |
| 2005/0070937 A1 | 3/2005 | Jambor et al. | |
| 2005/0283180 A1 | 12/2005 | Conlon | |
| 2007/0249893 A1* | 10/2007 | Krumme | 600/31 |
| 2010/0305397 A1* | 12/2010 | Birk et al. | 600/37 |
| 2011/0071646 A1* | 3/2011 | Dlugos et al. | 623/23.64 |
| 2011/0184229 A1* | 7/2011 | Raven et al. | 600/37 |

OTHER PUBLICATIONS

K.J. Mortele, P. Pattijn, P. Mollet, F. Berrevoet, U. Hesse, W. Ceelen, P.R. Ros, The Swedish Laparoscopic Adjustable Gastric Banding for Morbid Obesity: Radiologic Findings in 218 Patients; American Journal of Roentgenology; Jul. 2001, pp. 77 through 84.

Notification of Transmittal of the International Search Report and the Written Opinion of the International Searching Authority, or the Declaration; Mar. 16, 2009.

International Application No. PCT/US2009/032536, International Preliminary Report on Patentability, dated Aug. 3, 2010, 5 pages.

* cited by examiner

GASTRIC INFLATION BAND WITH INTEGRATED INFUSION CATHETER

RELATED APPLICATIONS

This application claims benefit of U.S. Provisional Application Ser. No. 61/024,603, filed Jan. 30, 2008, entitled "Gastric Inflation Band with Integrated Infusion Catheter," which is incorporated herein by reference.

FIELD OF THE INVENTION

This invention relates to a device for the treatment of obesity, and, more specifically, to an inflatable band that can be surgically placed around the stomach while also providing a means for direct drug and therapeutic agent delivery to the site of band placement.

BACKGROUND OF THE INVENTION

One method to treat obesity is to place an inextensible band on the outside of a portion of the patient's stomach thereby creating a stoma with reduced diameter which restricts the patient's food intake. Kuzmak et al. describes a gastric banding device in U.S. Pat. No. 4,592,339, which is made of inextensible material and needs to be surgically tightened to achieve the desired diameter of the stoma opening. The Kuzmak band also provides an inflatable portion that allows small post-operational adjustment of the diameter of the stoma after implantation by injection or withdrawal of fluid from an implanted injection port. U.S. Pat. No. 5,601,604 issued to Vincent describes a gastric band that incorporates a fastening means and an inflatable inner surface that allows a more versatile range of adjustment to the stoma.

Patients undergoing gastric banding procedures using existing gastric banding devices are at risk for certain complications, such as inflammation of the stomach at the site of band placement, infection of the band, and band erosion. Band erosion is sometimes associated with inflammation and infection after the surgical placement of the band. Patients with inflammation and infection are usually treated with systematic administration of large doses of anti-inflammatory agents or antibiotics. However, in many cases, dosage of drugs or therapeutic agents large enough to achieve an effective concentration at the band placement site may not be feasible or desirable. Treatment of such complications may require surgical band removal. Existing gastric banding devices that incorporate a continuous inflatable inner surface sometimes pinch and fold in practice, and may contribute to the inflammation and irritation of the surrounding stomach tissue at the band placement site. There exists a demand for a gastric band that avoids the short comings of existing gastric bands and also provides a means to deliver drug or therapeutic agents directly to the site of the band placement.

SUMMARY OF THE INVENTION

The present invention is an inflatable gastric band that incorporates a fluid channel located proximate to or within an outer surface of the band, and an inflatable bladder on a stomach-facing side of the band. The gastric band attaches to a double lumen catheter, with one of the lumens communicating with the fluid channel and the other lumen communicating with the inflatable bladder. Each lumen also communicates with a respective chamber of a dual infusion port. Injection or withdrawal of fluid in one chamber of the infusion port allows adjustment of the diameter of the stoma, by expanding/contracting the inflatable bladder, while the injection of drugs or therapeutic agents into the other chamber allows the infusion of drugs or agents directly into the abdominal cavity of a gastric band recipient. The inflatable bladder can be continuous or segmented. A segmented bladder reduces the possibility of a pinching and/or a folding of the inner surface of the gastric band during expansion/contraction, thereby lessening a chance of stomach pinching or irritation.

BRIEF DESCRIPTION OF THE DRAWINGS

The present invention will be better understood with reference to the following description taken in combination with the drawings, in which.

DETAILED DESCRIPTION OF THE INVENTION

The present invention provides an adjustable gastric band adapted for placement by laparoscopic surgery around a patient's stomach. The gastric band provides for delivery of therapeutic agents directly to the band placement site. Additionally, the present invention provides a configuration of an inflatable bladder that avoids folds and pinches, thereby reducing the possibility of stomach irritation.

Figure 1A:
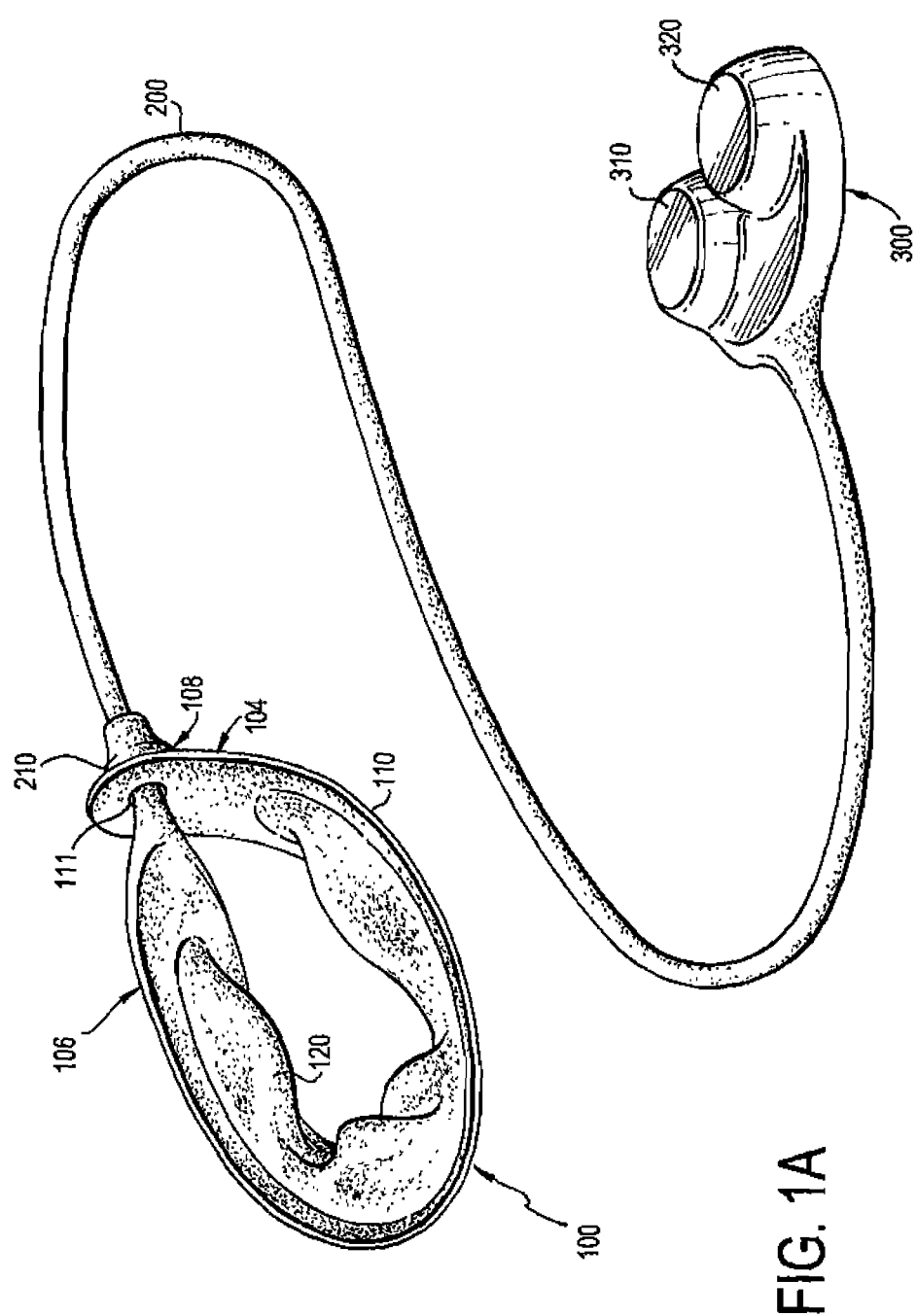
FIG. 1A is a schematic drawing of a gastric inflatable band according to one embodiment of the present invention.

FIG. 1A provides a prospective view of one embodiment of the present invention. The device comprises a band portion 100, a catheter portion 200, and a two chambered infusion port 300. The band portion 100 comprises an outer band member 110 and an inner inflatable bladder 120. The outer band member 110 is made of a tissue compatible material that is flexible, but preferably not extensible. The inner inflatable bladder 120 is also made of tissue compatible material that is elastic. The inflatable bladder 120 can be filled with fluid, such as saline. The band portion 100 further comprises a head end 104 and a tail end 106. The head end 104 comprises a locking mechanism 108 to receive the tail end 106. In the embodiment shown in FIG. 1A, the locking mechanism 108 comprises a hole 111 cut precisely in the outer band member 110. The tail end 106 comprises a retaining ring 210 that engages the locking mechanism 108 on the head end 104. During surgical placement of the gastric band, the catheter portion 200 is pulled through the hole 111 in the outer band member 110 until the retaining ring 210 emerges on the other side of the outer band member 110 and locks in place. When locked, the band portion 100 forms a ring with fixed diameter around the patient's stomach. The inflatable bladder 120 is adapted to expand or subsequently contract (deflate) depending on the amount of fluid delivered thereto. Infusion to or withdrawal of fluid from the inflatable bladder 120 allows for easy adjustment of an inner diameter of the band portion 100. This, in turn, adjusts the diameter of the stoma of the patient's stomach.

Figure 1B:
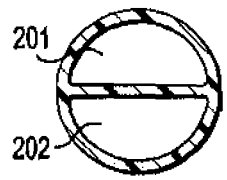
FIG. 1B is an exemplary cross-section of a catheter portion of the invention shown in FIG. 1A.

The band portion 100 communicates with the infusion port 300 through the catheter portion 200. The catheter portion 200 comprises two lumens 201, 202. FIG. 1B shows a cross-section view of one embodiment of the catheter portion 200, illustrating that the two internal lumens 201, 202 each have a "D" shaped configuration. In other embodiments of the present invention, the lumens 201, 202 can be configured to any desired shape presently known in the catheter art. The catheter portion 200 of present invention may also include more than two lumens. The first lumen 201 is in fluid tight communication, on one end, with the inflatable bladder 120 and on the other end is in fluid tight communication with a first chamber 310 of the infusion port 300. The amount of fluid within the inflatable bladder 120 can thus be adjusted by injecting or withdrawing fluid from the corresponding chamber 310 of infusion port 300, thereby controlling the inner diameter of the band portion 100.

Figure 1C:
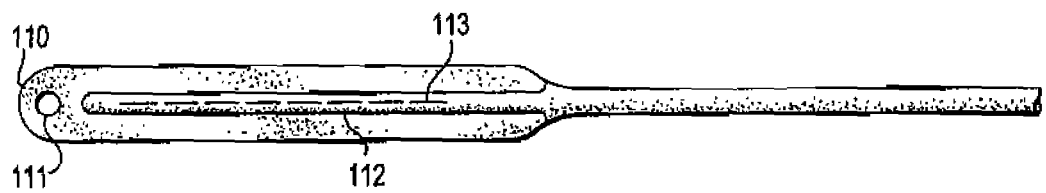
FIG. 1C is a schematic top view of an outer band side of a band portion of the invention shown in FIG. 1A.

FIG. 1C shows a top view of the band portion 100 of the present invention. The outer band member 110 further comprises a fluid channel 112 approximate to the outer surface of the band member 110. Openings such as slits or holes are formed in the outer wall of the fluid channel 112. In one embodiment, the outer wall of the fluid channel 112 is made of a flexible material that is essentially flat and uniform in thickness. Slits 113 are precisely cut into the outer wall of the fluid channel 112. These slits 113 are essentially one-way valves that open and allow free communication of fluid inside of the fluid channel 112 to the abdominal cavity when the hydrostatic pressure inside the fluid channel is higher than a predetermined threshold compared to the outside pressure. When the pressure in the abdominal cavity is equal or higher than the fluid pressure inside the fluid channel 112, the slits 113 close and prevent retrograde fluid flow into the fluid channel 112. The minimum amount of pressure needed to open the slits may be adjusted by varying the number of slits, length of the slits, the thickness and/or elasticity of the fluid channel wall.

Figure 1D:
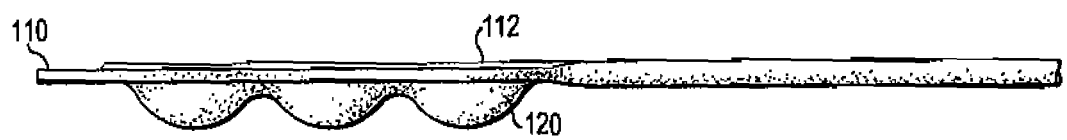
FIG. 1D is a schematic side view of the outer band side of the band portion of the invention shown in FIG. 1C.
Figure 1E:
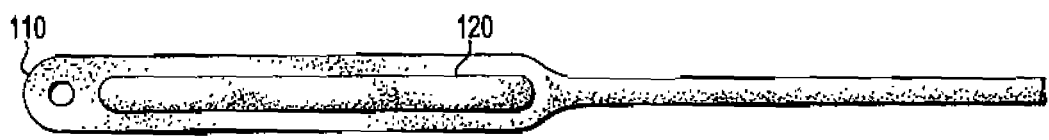
FIG. 1E is a schematic bottom view of an inner band side of the band portion of the invention shown in FIG. 1C.
Figure 1F:
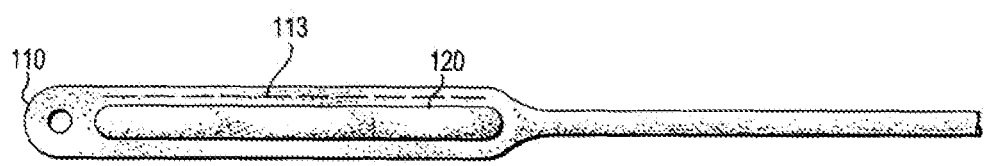
FIG. 1F is a schematic bottom view of an inner band side of a band portion of another exemplary embodiment of the present invention.
Figure 1G:
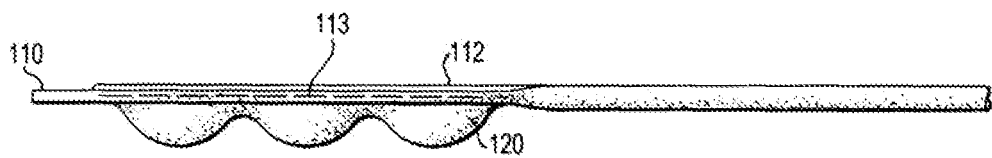
FIG. 1G is a schematic side view of an outer band side of a band portion of yet another exemplary embodiment of the present invention.

Although FIG. 1C shows the slits or holes 113 only on the outer side of the band portion 100 (i.e., the side opposite the inflatable bladder 120), the fluid channel 112 could be configured so that the slits or holes 113 open to the inner side of the band portion 100, as illustrated in FIG. 1F, or to the longitudinal edges, as illustrated in FIG. 1G. In another embodiment of the invention, the fluid channel 112 may be integral to, or exist essentially within, the band member 110, thereby allowing slits or holes to be located variously about the inner and outer sides, as well as along the edges, of the band member 110. Alternatively, in a further embodiment, the fluid channel 112 comprises a permeable material along at least a portion of its respective longitudinal length, allowing the drugs or agents introduced into the fluid channel 112 to pass through the permeable portion of the channel 112 when a hydrostatic pressure inside the channel 122 is greater than a predetermined threshold, such as the pressure within the abdominal cavity. The permeable material may be a material selectively permeable to drugs and therapeutic agents. The permeable material can be configured into a membrane. Permeability could be controlled by the material composition, thereby allowing selective passage of drugs and therapeutic agents through the membrane based on pre-selected criteria, such as the molecular weight.

The second lumen 202 of the catheter portion 200 is in fluid tight communication with, on one end, the fluid channel 112 of band member 110 and, at the other end, a second chamber 320 of the infusion port 300. Injection of drugs or a therapeutic agent into the second chamber 320 of the infusion port 300 allows the delivery of the drugs or therapeutic agents directly to the site of band portion 100 placement. This allows localized administration of drugs and therapeutic agents to the placement site of the gastric band, minimizing the total dosage of drugs or therapeutic agents required, if administered differently, and reducing the risk of systematic adverse reactions to the drugs or therapeutic agents.

FIG. 1A represents another feature of the infusion port 300 included in one embodiment of the present invention. The two chambers 310, 320 of the infusion port 300 are of different heights. The height difference of the two chambers 310, 320 is distinguishable by tactile examination. When the infusion port 300 is implanted in a patient, a physician can readily distinguish the two infusion chambers 310, 320 by palpitation of the implant site without the aid of any other instrument.

FIG. 1D shows a side view of the band portion 100 of the present invention. FIG. 1E shows a bottom view of the band portion 100 of the present invention. In both views, the segmented inflation bladder 120 aspect of the present invention is shown. In this aspect, the inflatable bladder 120 is configured into several segments. A segmented inflatable bladder 120 can expand to a greater degree than a continuous inflation bladder retaining the same amount of fluid. A segmented inflation bladder thereby provides a greater degree of post-surgical adjustment to the size of the stoma in the patient's stomach. Another advantage provided by a segmented bladder is that only the smooth, middle portion of each segment contacts the stomach. This avoids many possible pinch points and fold areas that would irritate the outer lining of the stomach, due to the lesser bladder contact area with the stomach.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

I claim:

1. A gastric band for treating obesity, the gastric band comprising:
a gastric band portion having an outer inextensible band member and an inner inflation bladder, the outer inextensible band member including a channel comprising an outer wall and at least one opening in the outer wall, the at least one opening providing for fluid communication between the channel and an abdominal cavity of a gastric band recipient;
an infusion port having a first chamber and a second chamber; and
a catheter portion having a first end attached to the band portion and a second end attached to the infusion port; the catheter portion including:
a first lumen in fluid communication with the inner inflation bladder and the first chamber of the infusion port, thereby allowing liquids introduced into the first chamber to expand the inner inflation bladder; and
a second lumen in fluid communication with the channel of the inextensible band member and the second chamber of the infusion port, thereby allowing liquids introduced into the second chamber to pass into the abdominal cavity of the gastric band recipient via the at least one opening.

2. The gastric band of claim 1, wherein the inflation bladder is segmented.

3. The gastric band of claim 2, wherein each segment expands convexly to be smooth and rounded, resembling an exterior of a sphere, and wherein the segments are configured along the band portion so that only the smooth, rounded middle portions of each segment contact a stomach of a gastric band recipient, thereby lessening inner inflation bladder contact area with the stomach and lessening stomach pinching or irritation.

4. The gastric band of claim 1, wherein the channel of the inextensible band member extends substantially an entire length of the inextensible band member.

5. The gastric band of claim 1, wherein the at least one opening in the channel is a plurality of slits extending longitudinally along the channel.

6. The gastric band of claim 5, wherein the slits are one-way valves that open to dispense fluid into the abdominal cavity when a hydrostatic pressure inside the channel is greater than a predetermined threshold.

7. The gastric band of claim 6, wherein the predetermined threshold is a pressure within the abdominal cavity.

8. The gastric band of claim 1, wherein the at least one opening is located on a side of the inextensible band member opposite the inflation bladder.

9. The gastric band of claim 1, wherein the at least one opening is located on a same side of the inextensible band member as the inflation bladder.

10. The gastric band of claim 1, wherein the at least one opening in the channel is a plurality of openings, some openings located on a side of the inextensible band member opposite the inflation bladder and some openings located on a same side of the inextensible band member as the inflation bladder.

11. The gastric band of claim 1, wherein the first chamber of the infusion port is of a different height than the second chamber of the infusion port.

12. The gastric band of claim 1, wherein the band portion further comprises a head end and a tail end, the head end comprising a locking means for receiving the tail end.

* * * * *